(12) United States Patent
Kogure et al.

(10) Patent No.: US 8,097,276 B2
(45) Date of Patent: Jan. 17, 2012

(54) METHOD FOR COATING PARTICLE WITH LIPID FILM

(75) Inventors: Kentaro Kogure, Hokkaido (JP); Arisa Minoura, Hokkaido (JP); Hideyoshi Harashima, Hokkaido (JP)

(73) Assignees: National University Corporation Hokkaido University, Hokkaido (JP); Shionogi & Co., Ltd., Osaka (JP)

( * ) Notice: Subject to any disclaimer, the term of this patent is extended or adjusted under 35 U.S.C. 154(b) by 851 days.

(21) Appl. No.: 11/795,513

(22) PCT Filed: Jan. 18, 2006

(86) PCT No.: PCT/JP2006/300603
§ 371 (c)(1),
(2), (4) Date: May 13, 2008

(87) PCT Pub. No.: WO2006/077857
PCT Pub. Date: Jul. 27, 2006

(65) Prior Publication Data
US 2009/0136563 A1 May 28, 2009

(30) Foreign Application Priority Data
Jan. 18, 2005 (JP) ................................. 2005-010998

(51) Int. Cl.
*A61K 9/127* (2006.01)
*A01N 25/26* (2006.01)
*G01N 33/00* (2006.01)

(52) U.S. Cl. ....................................... 424/450; 424/417

(58) Field of Classification Search .......................... None
See application file for complete search history.

(56) References Cited

U.S. PATENT DOCUMENTS

| 4,078,052 A * | 3/1978 | Papahadjopoulos .......... 424/450 |
| 4,839,175 A | 6/1989 | Guo et al. |
| 5,616,341 A | 4/1997 | Mayer et al. |
| 5,908,777 A * | 6/1999 | Lee et al. .................... 435/320.1 |
| 5,981,501 A * | 11/1999 | Wheeler et al. ............. 514/44 R |
| 2003/0049158 A1 | 3/2003 | Hui et al. |

FOREIGN PATENT DOCUMENTS

| JP | 2-500360 | 2/1990 |
| JP | 2-502458 | 8/1990 |
| JP | 2004-532068 | 10/2004 |

OTHER PUBLICATIONS

Lee et al. Folate-targeted, anionic liposome-entrapped polylysine-condensed DNA for tumor cell-specific gene transfer. J. Biol. Chem. 271:8481-8487, 1996.*
Kogure et al. Development of a non-viral multifunctional envelope-type nano device by a novel lipid film hydration method. J. Controlled Release 98:317-323, 2004.*
Sasaki et al. Construction of a multifunctional envelope-type nano device by a SUV-fusion method. International Journal of Pharmaceutics 296:142-150, 2005.*
Mozafari et al. Mechanism of calcium ion induced multilamellar vesicle-DNA interaction. J. Microencapsulation 15:55-65, 1998.*

* cited by examiner

*Primary Examiner* — Quang Nguyen
(74) *Attorney, Agent, or Firm* — Peter F. Corless; Christine C. O'Day; Edwards Wildman Palmer LLP

(57) ABSTRACT

A method for coating an object, i.e. a particle, with two sheets of lipid film having a space formed there between. In the method for coating a particle having a positive electrostatic-charging property with two sheets of lipid film, the particle having a positive electrostatic-charging property is brought into contact with a plurality of SUV type liposomes having a negative electrostatic-charging property to form a complex having a negative electrostatic-charging property containing the particle having a positive electrostatic-charging property and the SUV type liposomes having a negative electrostatic-charging property coupled electrostatically with the particle having a positive electrostatic-charging property, and then the complex having a negative electrostatic-charging property is treated with cation.

4 Claims, 3 Drawing Sheets

METHOD FOR COATING PARTICLE WITH LIPID FILM

TECHNICAL FIELD

The present invention relates to a method for coating a particle with lipid membranes.

BACKGROUND ART

In recent years, developments of vectors for delivering drugs, nucleic acids, peptides, proteins, sugars and the like certainly to target sites have been actively carried out. For example, for gene therapy, viral vectors such as retrovirus, adenovirus, adeno-associated virus and the like have been developed as vectors for introducing a desired gene to a target cell. However, since the viral vectors have problems such as difficulties in mass production, antigenicity, toxicity and the like, liposome vectors, which suffer less from such problems, have attracted attention. The liposome vectors have an advantage that the directivity to a target site can be enhanced by introducing functional molecules such as antibodies, proteins, sugar chains and the like to the surface of the liposome vectors.

As a method for preparing liposomes, for example, there is known a lipid film hydration method. According to the lipid film hydration method, multilamellar liposomes encapsulating an object material can be prepared by hydrating a lipid membrane in the presence of the object material such as genes (see Non-Patent Document 1). New lipid membranes can be further laminated on the external side of the multilamellar liposomes by repeatedly applying the lipid film hydration method to the multilamellar liposomes thus prepared. As such, by repeating the lipid film hydration method, the number of the lipid membranes included in the multilamellar liposomes can be increased.

[Non-Patent Document 1] Kogure, et al., Journal of Controlled Release, Vol. 98, pp. 317-323 (2004)

DISCLOSURE OF THE INVENTION

Problems to be Solved by the Invention

However, in the conventional methods such as the lipid film hydration method, since the lipid membranes are laminated non-uniformly, it was difficult to control the number of the lipid membranes to be included in multilamellar liposomes. Furthermore, in the conventional methods such as the lipid film hydration method and the like, lipid membranes can only be piled up onto any layer as in the case of geological strata, and thus it has been difficult to form a space in between the lipid membranes.

Therefore, it is an object of the present invention to provide a method for coating a subject particle with two sheets of lipid membrane having a space formed there between, and liposomes obtained by coating a subject particle with two sheets of lipid membrane by the method.

Means for Solving the Problems

A first method of the present invention is a method for coating a positively charged particle with two sheets of lipid membrane, comprising contacting the positively charged particle with a plurality of negatively charged SUV type liposomes to form a negatively charged complex containing the positively charged particle and the negatively charged SUV type liposomes that are electrostatically bound to the positively charged particle, and treating the negatively charged complex with cations.

According to the first method of the present invention, a positively charged particle can be coated with two sheets of lipid membrane having a space formed there between. In the liposome obtained by coating a positively charged particle by the first method of the present invention, there is formed a space between the two sheets of lipid membrane which coat the positively charged particle (the first lipid membrane formed on the external side of the positively charged particle, and the second lipid membrane formed on the external side of the first lipid membrane), and a desired material can be retained in this space.

According to the first method of the present invention, it is preferable that the positively charged particle is an aggregate of the object material. In this case, a bilamellar liposome encapsulating an aggregate of an object material and having a space formed between the two sheets of lipid membrane which coat the aggregate of object material, can be produced.

According to the first method of the present invention, it is preferable that the positively charged particle is a positively charged n-lamellar liposome, wherein n is an integer of 1 or greater. In this case, a (n+2)-lamellar liposome having a space formed between two sheets of lipid membranes that coat the positively charged n-lamellar liposome, can be produced.

According to the first method of the present invention, it is preferable that the positively charged particle has a zeta potential of 20 to 30 mV, while the negatively charged SUV type liposome has a zeta potential of −20 to −30 mV. In this case, a negatively charged complex containing a positively charged particle and a plurality of negatively charged SUV type liposomes that are electrostatically bound to the positively charged particle, can be efficiently formed.

According to the first method of the present invention, it is preferable that the positively charged particle has a particle diameter of 50 nm or larger. In this case, a negatively charged complex containing a positively charged particle and a plurality of negatively charged SUV type liposomes that are electrostatically bound to the positively charged particle, can be efficiently formed.

The second method of the present invention is a method for coating a negatively charged particle with two sheets of lipid membrane, comprising contacting the negatively charged particle with a plurality of positively charged SUV type liposomes to form a positively charged complex containing the negatively charged particle and the positively charged SUV type liposomes that are electrostatically bound to the negatively charged particle, and treating the positively charged complex with anions.

According to the second method of the present invention, the negatively charged particle can be coated with two sheets of lipid membrane having a space formed there between. In the liposome obtained by coating a negatively charged particle by the second method of the present invention, there is formed a space between the two sheets of lipid membrane which coat the negatively charged particle (the first lipid membrane formed on the external side of the negatively charged particle, and the second lipid membrane formed on the external side of the first lipid membrane), and a desired material can be retained in this space.

According to the second method of the present invention, it is preferable that the negatively charged particle is an aggregate of the desired material. In this case, a bilamellar liposome encapsulating an aggregate of an object material and having a space formed between the two sheets of lipid membrane which coat the aggregate of object material, can be produced.

According to the second method of the present invention, it is preferable that the negatively charged particle is a negatively charged n-lamellar liposome, wherein n is an integer of or greater. In this case, an (n+2)-lamellar liposome having a space formed between two sheets of lipid membrane that coat a negatively charged n-lamellar liposome, can be produced.

According to the second method of the present invention, it is preferable that the negatively charged particle has a zeta potential of −20 to −30 mV, while the positively charged SUV type liposome has a zeta potential of 20 to 30 mV. In this case, a positively charged complex containing a negatively charged particle and a plurality of positively charged SUV type liposomes that are electrostatically bound to the negatively charged particle, can be efficiently formed.

According to the second method of the present invention, it is preferable that the negatively charged particle has a particle diameter of 50 nm or larger. In this case, a positively charged complex containing a negatively charged particle and a plurality of positively charged SUV type liposomes that are electrostatically bound to the negatively charged particle can be efficiently formed.

Effects of the Invention

According to the method of the present invention, the subject particle for coating can be coated with two sheets of lipid membrane having a space formed there between. Therefore, if an aggregate of an object material is used as the subject particle for coating, a bilamellar liposome encapsulating the aggregate of object material and having a space formed between the two sheets of lipid membranes which coat the aggregate of object material can be produced; while if an n-lamellar liposome, wherein n is an integer of 1 or greater, is used as the subject particle for coating, an (n+2)-lamellar liposome having a space formed between two sheets of lipid membrane that coat the n-lamellar liposome, can be produced. In the liposome obtained by coating a positively charged particle or a negatively charged particle by the method of the present invention, there is formed a space between the two sheets of lipid membrane that coat the positively charged particle or negatively charged particle, and a desired material can be retained in this space.

BEST MODE FOR CARRYING OUT THE INVENTION

Figure 1:
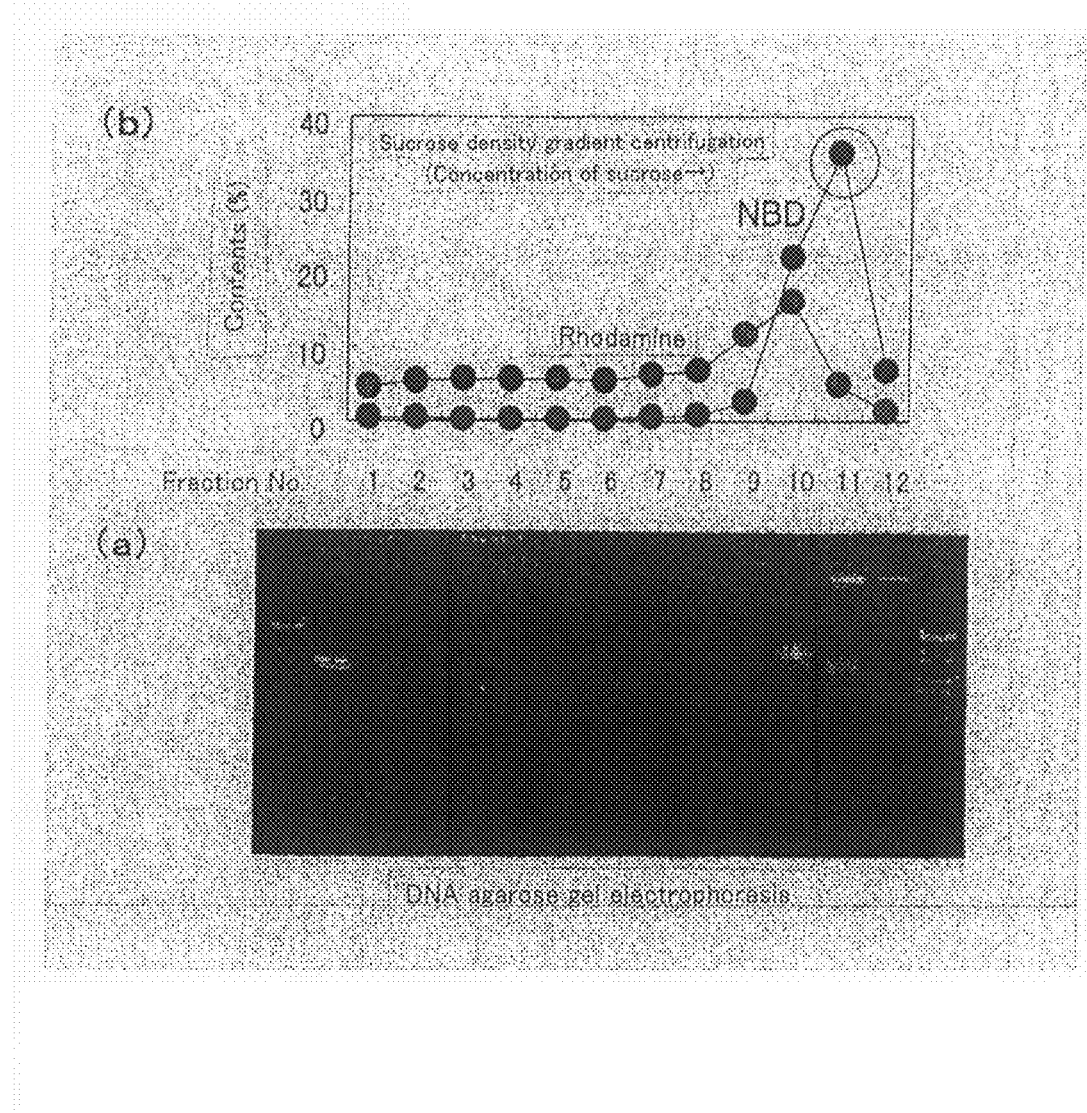
FIG. 1(a) is a photograph showing the results of measuring the DNA contents in each fraction by DNA agarose gel electrophoresis.
FIG. 1(b) is a graph showing the results of measuring the rhodamine contents and NBD contents in each fraction by means of fluorescence intensity.

In the first method of the present invention, first, a positively charged particle is contacted with a plurality of negatively charged SUV type liposomes to form a negatively charged complex containing the positively charged particle and the negatively charged SUV type liposomes that are electrostatically bound to the positively charged particle.

In the second method of the present invention, first, a negatively charged particle is contacted with a plurality of positively charged SUV type liposomes to form a positively charged complex containing the negatively charged particle and the positively charged SUV type liposomes that are electrostatically bound to the negatively charged particle.

The zeta potential of the positively charged particle is not particularly limited as long as the value is positive, but the value is usually 10 to 60 mV, preferably 20 to 50 mV, and more preferably 20 to 30 mV. The zeta potential of the negatively charged particle is not particularly limited as long as the value is negative, but the value is usually −10 to −60 mV, preferably −20 to −50 mV, and more preferably −20 to −30 mV. The conditions for the measurement of zeta potential are not particularly limited, but the temperature condition is usually 25° C.

The particle diameter of the positively charged particle and the negatively charged particle is not particularly limited, but the lower limit value of the particle diameter is preferably 50 nm, and more preferably 70 nm, while the upper limit value of the particle diameter is preferably 500 nm, more preferably 200 nm. If the particle diameter of the positively charged particle is within the above-mentioned range, the positively charged particle can be efficiently coated with two sheets of lipid membrane when the negatively charged SUV type liposomes that are electrostatically bound to the positively charged particle are treated with cations. Further, if the particle diameter of the negatively charged particle is within the above-mentioned range, the negatively charged particle can be efficiently coated with two sheets of lipid membrane when the positively charged SUV type liposomes that are electrostatically bound to the negatively charged particle are treated with an ions.

The positively charged particle may contain a neutral material and/or an anionic material in addition to a cationic material, as long as the particle is positively charged as a whole. The negatively charged particle may contain a neutral material and/or a cationic material, in addition to an anionic material, as long as the particle is negatively charged as a whole.

As the positively charged or negatively charged particle, for example, an aggregate of an object material (for example, a material to be delivered into a cell or a nucleus) can be used. In the case of using an aggregate of an object material as the positively charged or negatively charged particle, a bilamellar liposome encapsulating the object material can be produced by coating the positively charged or negatively charged particle with two sheets of lipid membrane. The aggregate of object material may be consisted of the object material alone, or alternatively may include materials other than the object material (for example, a carrier retaining the object material).

In the case where the object material is positively charged, an aggregate of the object material can be prepared, for example, by allowing the object material to be electrostatically bound to an anionic material to form a complex. In the case where the object material is negatively charged, an aggregate of the object material can be prepared, for example, by allowing the object material to be electrostatically bound to a cationic material to form a complex. If the object material is charged neither negatively nor positively, an aggregate of the object material can be prepared by allowing the object material to be bound to a cationic material by any appropriate manner (for example, physical adsorption, hydrophobic bonding, chemical bonding and the like) to form a complex.

Upon the formation of the complex, an aggregate of the object material which is either positively or negatively charged as a whole can be prepared, by adjusting the mixing ratio between the object material and a cationic material or an anionic material.

The object material is not particularly limited, and examples thereof include nucleic acid, peptide, protein, drug, sugar, complexes thereof, and the like. In addition, the term "nucleic acid" includes DNA or RNA, as well as analogues or derivatives thereof (for example, peptide nucleic acid (PNA), phosphorothioate DNA). Also, the nucleic acid may be of a single strand or a double strand, and may be either linear or cyclic.

If the object material is a nucleic acid, an aggregate of the nucleic acid can be prepared by allowing the nucleic acid to be electrostatically bound to a cationic material to form a complex. Upon the formation of the complex, an aggregate of nucleic acid which is either positively or negatively charged as a whole can be prepared, by adjusting the mixing ratio between the nucleic acid and the cationic material.

The cationic material used for preparing the aggregate of object material is not particularly limited as long as it is a material having a cationic group in the molecule. Examples of the cationic material that can be used include cationic lipids (for example, Lipofectamine (Invitrogen, Inc.)); polymers having cationic groups; homopolymers or copolymers of basic amino acids such as polylysine, polyarginine, copolymers of lysine and arginine, or derivatives thereof (for example, stearylated derivatives); polycationic polymers such as polyethyleneimine, poly(arylamine), poly(diaryldimethylammonium chloride), glucosamine; protamine sulfate; and the like. The number of cationic groups carried by the cationic material is not particularly limited, but the number is preferably two or more. The cationic group is not particularly limited as long as it can be positively charged, and examples thereof include an amino group; a monoalkylamino group such as a methylamino group, an ethylamino group; a dialkylamino group such as a dimethylamino group, a diethylamino group; an imino group; a guanidine group; and the like.

The anionic material that is used for preparing the aggregate of object material is not particularly limited as long as it is a material having an anionic group in the molecule. Examples of the anionic material that can be used include anionic lipids; polymers having anionic groups; homopolymers or copolymers of acidic amino acid such as polyaspartic acid, or derivatives thereof; polyanionic polymers such as xanthane gum, carboxyvinyl polymers, carboxymethylcellulose polystyrenesulfonic acid salts, polysaccharides, carrageenan; and the like. The number of anionic groups carried by the anionic material is not particularly limited, but the number is preferably two or more. The anionic group is not particularly limited as long as it can be negatively charged, and examples thereof include a functional group having a terminal carboxyl group (for example, a succinic acid residue, a malonic acid residue, etc.), a phosphate group, a sulfate group, and the like.

As the positively charged or negatively charged particle, for example, a positively charged or negatively charged n-lamellar liposome, wherein n is an integer of 1 or greater), can be used. In the case of using the n-lamellar liposome as the positively charged or negatively charged particle, a (n+2)-lamellar liposome can be produced by coating the positively charged or negatively charged particle with two sheets of lipid membrane. The positively charged or negatively charged n-lamellar liposome may or may not encapsulate an object material (for example, a material to be delivered into a cell or a nucleus) inside the liposome. The positively charged n-lamellar liposome may contain a neutral material and/or an anionic material in addition to a cationic material, as long as the liposome is positively charged as a whole. The negatively charged n-lamellar liposome may contain a neutral material and/or a cationic material in addition to an anionic material, as long as the liposome is negatively charged as a whole.

The n-lamellar liposome can be produced using known methods such as, for example, a hydration method, an ultrasonication method, an ethanol injection method, an ether injection method, a reverse phase evaporation method, a surfactant method, a freeze-thawing method. The n-lamellar liposome can also be prepared by coating a positively charged or negatively charged particle with two sheets of lipid membrane using the method of the present invention.

The positively charged or negatively charged n-lamellar liposome can be produced by adjusting the type and content of the material constituting the n-lamellar liposome (for example, the lipid membrane-constituting component, the material being encapsulated inside the liposome). Furthermore, a positively charged n-lamellar liposome can be produced by modifying the surface of a negatively charged n-lamellar liposome or a neutral n-lamellar liposome with a cationic material, while a negatively charged n-lamellar liposome can be produced by modifying the surface of a positively charged n-lamellar liposome or a neutral n-lamellar liposome with an anionic material.

The n-lamellar liposome can be produced by, for example, a hydration method as follows. Components of lipid membrane are dissolved in an organic solvent, and then the organic solvent is removed by evaporation to obtain a lipid membrane. Here, the organic solvent may be exemplified by a hydrocarbon such as pentane, hexane, heptane, cyclohexane; a halogenated hydrocarbon such as methylene chloride, chloroform; an aromatic hydrocarbon such as benzene, toluene; a lower alcohol such as methanol, ethanol; an ester such as methyl acetate, ethyl acetate or the like; a ketone such as acetone; or the like, and these can be used individually or in combination of two or more species. Subsequently, the lipid membrane is hydrated, and agitated or ultrasonicated, thereby converting the lipid membrane to multilamellar liposomes. The conversion of multilamellar liposome to unilamellar liposome, or the conversion of unilamellar liposome to multilamellar liposome can be carried out according to known methods. When n-lamellar liposomes are passed through a filter having a predetermined pore size, n-lamellar liposomes having a constant particle size distribution can be obtained.

When the object material is water-soluble, the object material can be encapsulated in the aqueous phase inside a liposome by adding the object material or aggregates thereof to the aqueous solvent used in hydrating a lipid membrane during the preparation of the n-lamellar liposome. When the object material is lipid-soluble, the object material can be encapsulated in the lipid membranes of a liposome by adding the object material or aggregates thereof to the organic solvent used during the preparation of the n-lamellar liposome.

When the surface of a negatively charged n-lamellar liposome or neutral n-lamellar liposome is modified with a cationic material, for example, a cationic material having a hydrophobic group is added to the liquid outside the negatively charged n-lamellar liposome or neutral n-lamellar liposome. In this way, the hydrophobic group is inserted into the lipid membrane such that the cationic material is exposed from the lipid membrane, and thus the cationic material can be introduced into the surface of the negatively charged liposome or neutral n-lamellar liposome.

When the surface of a positively charged n-lamellar liposome or neutral n-lamellar liposome is modified with an anionic material, for example, an anionic material having a hydrophobic group is added to the liquid outside the positively charged n-lamellar liposome or neutral n-lamellar liposome. In this way, the hydrophobic group is inserted into the lipid membrane such that the anionic material is exposed from the lipid membrane, and thus the anionic material can be introduced into the surface of the positively charged liposome or neutral n-lamellar liposome.

The hydrophobic group is not particularly limited as long as it can be inserted into the lipid membrane. Examples of the hydrophobic group include saturated or unsaturated fatty acid groups such as stearyl group, sterol residues such as cholesterol residue, phospholipid residues, glycolipid residues, long chain aliphatic alcohol residues (for example, phosphatidylethanolamine residue), polyoxypropylenealkyl group, glycerin fatty acid ester residues, and the like, and among these, fatty acid groups having 10 to 20 carbon atoms (for example, a palmitoyl group, an oleyl group, a stearyl group, an arachidoyl group, etc.) are particularly preferred.

The lipid membrane component for the n-lamellar liposome is not particularly limited as long as the component does not inhibit the formation of lipid bilayer, and examples of the lipid membrane component include lipids, membrane-stabilizing agents, antioxidants, charged materials, membrane proteins and the like.

The type and content of the lipid membrane component for a positively charged n-lamellar liposome are controlled such that the n-lamellar liposome is positively charged as a whole, while the type and content of the lipid membrane component for a negatively charged n-lamellar liposome are controlled such that the n-lamellar liposome is negatively charged as a whole. Examples of the lipid membrane component which imparts a positive charge include cationic lipids, cationic membrane-stabilizing agents and the like, while examples of the lipid membrane component which imparts a negative charge include an ionic lipids, anionic membrane-stabilizing agents and the like. Moreover, in the case where a predetermined material (for example, an aggregate of the object material) is encapsulated inside the n-lamellar liposome, the type and content of the lipid membrane component in the n-lamellar liposome are controlled in consideration of the overall charge of the material encapsulated inside the n-lamellar liposome.

An SUV (small unilamellar vesicle) type liposome is a unilamellar liposome having a particle size (diameter) of 100 nm or less. The particle size (diameter) of the SUV type liposome is not particularly limited as long as it is of 100 nm or less, but the size is typically 30 to 100 nm, preferably 30 to 70 nm, and more preferably 30 to 50 nm.

Since a multilamellar liposome (MLV) and a unilamellar liposome other than SUV (for example, LUV (large unilamellar vesicle), GUV (giant unilamellar vesicle), etc.) have a particle diameter of 100 nm or greater (in general, a lipid membrane having a particle diameter of 100 nm or greater is considered as a planar membrane), the curvature and surface energy of the membrane are small, and aggregation between liposomes is hard to occur. In this regard, since a SUV type liposome has a particle diameter of less than 100 nm, the curvature and surface energy of the membrane are large, and aggregation between liposomes readily occurs. Therefore, when negatively charged SUV type liposomes that are electrostatically bound to a positively charged particle are treated with cations, it is possible to efficiently induce membrane fusion between the negatively charged SUV type liposomes. Further, when positively charged SUV type liposomes which are electrostatically bound to a negatively charged particle are treated with anions, it is possible to efficiently induce membrane fusion between the positively charged SUV type liposomes.

SUV type liposomes can be produced, for example, by an ultrasonication method as follows. The lipid membrane components are dissolved in an organic solvent, and then the organic solvent is removed by evaporation to obtain a lipid membrane. Here, the organic solvent may be exemplified by a hydrocarbon such as pentane, hexane, heptane, cyclohexane; a halogenated hydrocarbon such as methylene chloride, chloroform; an aromatic hydrocarbon such as benzene, toluene; a lower alcohol such as methanol, ethanol; an ester such as methyl acetate, ethyl acetate; a ketone such as acetone; or the like, and these can be used individually or in combination of two or more species. Subsequently, the lipid membrane is hydrated, and agitated or ultrasonicated using an ultrasonic bath, thereby producing multilamellar liposomes. The resulting multilamellar liposomes are further ultrasonicated by means of a probe type ultrasonicator, and thus SUV type liposomes which are small unilamellar liposomes can be prepared.

The lipid membrane component for the SUV type liposome is not particularly limited as long as the component does not inhibit the formation of lipid bilayer, and examples of the lipid membrane component include lipids, membrane stabilizing agents, antioxidants, charged materials, membrane proteins.

The type and content of the lipid membrane component in the positively charged SUV type liposome are controlled such that the SUV type liposome is positively charged as a whole, while the type and content of the lipid membrane component in the negatively charged SUV type liposome are controlled such that the SUV type liposome is negatively charged as a whole. Examples of the lipid membrane component which imparts a positive charge include cationic lipids, cationic membrane-stabilizing agents and the like, while examples of the lipid membrane component which imparts a negative charge include anionic lipids, anionic membrane-stabilizing agents and the like. The positively charged SUV type liposome may contain a lipid membrane component which imparts a negative charge and/or a neutral lipid membrane component, in addition to the lipid membrane component which imparts a positive charge, as long as the liposome is positively charged as a whole. The negatively charged SUV type liposome may contain a lipid membrane component which imparts a positive charge and/or a neutral lipid membrane component, in addition to the lipid membrane component which imparts a negative charge, as long as the liposome is negatively charged as a whole.

When the positively charged SUV type liposome contains a cationic lipid as the lipid membrane component which imparts a positive charge, the blending amount of the cationic lipid is usually 5 to 30% (molar ratio), preferably 10 to 20% (molar ratio), and more preferably 10 to 15% (molar ratio), based on the total blending amount of lipids.

When the negatively charged SUV type liposome contains an anionic lipid as the lipid membrane component which imparts a negative charge, the blending amount of the anionic lipid is usually 5 to 30% (molar ratio), preferably 10 to 20% (molar ratio), and more preferably 10 to 15% (molar ratio), based on the total compounding amount of lipids.

The zeta potential of the positively charged SUV type liposome is not particularly limited as long as it is positive, but the zeta potential is usually 10 to 60 mV, preferably 20 to 50 mV, and more preferably 20 to 30 mV. The zeta potential of the negatively charged SUV type liposome is not particularly limited as long as it is negative, but the zeta potential is usually 10 to 60 mV, preferably 20 to 50 mV, and more preferably 20 to 30 mV. The conditions for the measurement of zeta potential are not particularly limited, but the temperature condition is usually 25° C.

With regard to the n-lamellar liposome or SUV type liposome, lipids are the essential component of the lipid membrane, and the blending amount is usually 30 to 100% (molar ratio), preferably 50 to 100% (molar ratio), and more preferably 70 to 100% (molar ratio), based on the total blending amount of the lipid membrane components.

Examples of the lipid include phospholipids, glycolipids, sterols, saturated or unsaturated fatty acids, and the like. Examples of the phospholipids include phosphatidylcholine (for example, dioleoylphosphatidylcholine, dilauroylphosphatidylcholine, dimyristoylphosphatidylcholine, dipalmitoylphosphatidylcholine, distearoylphosphatidylcholine, etc.), phosphatidylglycerol (for example, dioleoylphosphatidylglycerol, dilauroylphosphatidylglycerol, dimyristoylphosphatidylglycerol, dipalmitoylphosphatidylglycerol, distearoylphosphatidylglycerol, etc.), phosphatidylethanolamine (for example, dioleoylphosphatidylethanolamine, dilauroylphosphatidylethanolamine, dimyristoylphosphatidylethanolamine, dipalmitoylphosphatidylethanolamine, distearoylphosphatidylethanolamine, etc.), phosphatidylserine, phosphatidylinositol, phosphatidic acid, cardiolipin, sphingomyelin, egg yolk lecithin, soybean lecithin, hydrogenation products thereof, and the like. Examples of the glycolipids include glyceroglycolipid (for example, sulfoxyribosyl glyceride, diglycosyl diglyceride, digalactosyl diglyceride, galactosyl diglyceride, and glycosyl diglyceride), sphingoglycolipid (for example, galactosyl cerebroside, lactosyl cerebroside and ganglioside), and the like. Examples of the sterols include animal-derived sterols (for example, cholesterol, cholesterol succinate, lanosterol, dihydrolanosterol, desmosterol and dihydrocholesterol), plant-derived sterols (phytosterol) (for example, stigmasterol, sitosterol, campesterol and brassicasterol), microorganism-derived sterols (for example, thymosterol and ergosterol), and the like. Examples of the saturated or unsaturated fatty acids include saturated or unsaturated fatty acids having 12 to 20 carbon atoms, such as palmitic acid, oleic acid, stearic acid, arachidonic acid, myristic acid.

The lipids are classified into neutral lipids, cationic lipids and anionic lipids. Examples of the neutral lipids include diacylphosphatidylcholine, diacylphosphatidylethanolamine, cholesterol, ceramide, sphingomyelin, cephalin, cerebroside and the like; examples of the cationic lipids include DODAC (dioctadecyldimethylammonium chloride), DOTMA (N-(2,3-dioleyloxy)propyl-N,N,N-trimethylammonium), DDAB (didodecylammonium bromide), DOTAP (1,2-dioleoyloxy-3-trimethylammonio propane), DC-Chol (3β-N—(N',N'-dimethyl-aminoethane)-carbamol cholesterol), DMRIE (1,2-dimyristoyloxypropyl-3-dimethylhydroxyethylammonium), DOSPA (2,3-dioleyloxy-N-[2-(sperminecarboxamido)ethyl]-N,N-dimethyl-1-propanaminium trifluoroacetate), and the like; and examples of the anionic lipids include cardiolipin, diacylphosphatidylserine, diacylphosphatidic acid, N-succinylphosphatidylethanolamine (N-succinyl-PE), phosphatidic acid, phosphatidylinositol, phosphatidylglycerol, phosphatidylethylene glycol, cholesterol succinate, and the like.

With regard to the n-lamellar liposome or SUV type liposome, the membrane-stabilizing agent is any component that is added to physically or chemically stabilize the lipid membrane, or to control the fluidity of the lipid membrane, and the blending amount is usually 10 to 50% (molar ratio), preferably 20 to 50% (molar ratio), and more preferably 30 to 50% (molar ratio), based on the total blending amount of the lipid membrane components.

Examples of the membrane-stabilizing agent include sterols, glycerin or its fatty acid esters. Specific examples of the sterol include those mentioned above, while examples of the fatty acid esters of glycerin include triolein, trioctanoin and the like.

With regard to the n-lamellar liposome or SUV type liposome, the antioxidant is any component that is added to prevent oxidation of the lipid membrane, and the blending amount is usually 5 to 30% (molar ratio), preferably 10 to 30% (molar ratio), and more preferably 20 to 30% (molar ratio), based on the total blending amount of the lipid membrane components.

Examples of the antioxidant include tocopherol, propyl gallate, ascorbyl palmitate, butylated hydroxytoluene and the like.

With regard to the n-lamellar liposome or SUV type liposome, the charged material is any component that is added to impart a positive charge or a negative charge to the lipid membrane, and the blending amount is usually 5 to 30% (molar ratio), preferably 10 to 20% (molar ratio), and more preferably 10 to 15% (molar ratio), based on the total blending amount of the lipid membrane component.

Examples of the charged material which imparts a positive charge include saturated or unsaturated aliphatic amines such as stearylamine, oleylamine; saturated or unsaturated cationic synthetic lipids such as dioleoyltrimethylammoniumpropane; and the like. Examples of the charged material which imparts a negative charge include dicetyl phosphate, cholesterol succinate, phosphatidylserine, phosphatidylinositol, phosphatidic acid, and the like.

With regard to the n-lamellar liposome or SUV type liposome, the membrane protein is any component that is added to maintain the structure of the lipid membrane, or to impart any functionality to the lipid membrane, and the blending amount is usually 0.1 to 2% (molar ratio), preferably 0.5 to 2% (molar ratio), and more preferably 1 to 2% (molar ratio), based on the total blending amount of the lipid membrane components.

Examples of the membrane protein include surface membrane proteins, inner membrane proteins and the like.

The conditions for contacting the negatively charged or positively charged SUV type liposomes with the positively charged or negatively charged particle, respectively, are not particularly limited, but the temperature is usually 10 to 40° C., and preferably 20 to 30° C.; the pH is usually 6.5 to 8.0, and preferably 7.0 to 7.5; and the time is usually 1 to 20 minutes, and preferably 5 to 10 minutes. The solvent used for the contacting is not particularly limited, but for example, HEPES buffer solution, physiological saline, sucrose solution and the like can be used. The amount of the negatively charged or positively charged SUV type liposomes dispersed in the solvent is usually an excess against the positively charged or negatively charged particle, and for example, the amount is 2- to 4-fold the amount of the negatively charged or positively charged SUV type liposomes that is theoretically required at minimum for the encapsulation of the positively charged or negatively charged particle.

When negatively charged SUV type liposomes are contacted with a positively charged particle, the positively charged particle and the negatively charged SUV type liposomes bind through electrostatic interaction, and the surface of the positively charged particle is covered with a plurality of negatively charged SUV type liposomes. Then, a negatively charged complex containing the positively charged particle and a plurality of negatively charged SUV type liposomes electrostatically bound to the positively charged particle is formed. Here, it is preferable that a negatively charged complex having a zeta potential of 20 to 50 mV is formed, and it is more preferable that a negatively charged complex having a zeta potential of 20 to 30 mV is formed. Then, the negatively charged SUV type liposomes that are electrostatically bound to the positively charged particle can be efficiently treated with cations. The zeta potential of the negatively charged complex can be controlled by controlling the zeta potential, particle diameter and the like of the positively charged particle and the negatively charged SUV type liposome.

When positively charged SUV type liposomes are contacted with a negatively charged particle, the negatively charged particle and the positively charged SUV type liposomes bind through electrostatic interaction, and the surface of the negatively charged particle is covered with a plurality of the positively charged SUV type liposomes. Then, a positively charged complex containing the negatively charged particle and a plurality of positively charged SUV type liposomes that are electrostatically bound to the negatively charged particle, is formed. Here, it is preferable that a positively charged complex having a zeta potential of 20 to 50 mV is formed, and it is more preferable that a positively charged complex having a zeta potential of 20 to 30 mV is formed. Then, the positively charged SUV type liposomes that are electrostatically bound to the negatively charged particle can be efficiently treated with anions. The zeta potential of the positively charged complex can be controlled by controlling the zeta potential, particle diameter and the like of the negatively charged particle and the positively charged SUV type liposomes.

In the first method of the present invention, the formed negatively charged complex is subsequently treated with cations.

In the second method of the present invention, the formed positively charged complex is subsequently treated with anions.

The cation is not particularly limited, and for example, a monovalent cation such as $H^+$; a divalent cation such as $Ca^{2+}$, $Mg^{2+}$; a trivalent cation such as $Al^{3+}$; and the like may be mentioned. Examples of the material generating $H^+$ include acids such as hydrochloric acid, acetic acid; examples of the material generating $Ca^{2+}$ include calcium chloride and the like; examples of the material generating $Mg^{2+}$ include magnesium chloride and the like; and examples of the material generating $Al^{3+}$ include aluminum chloride and the like.

The anion is not particularly limited, and for example, $OH^-$, $SO_4^{2-}$, $PO_4^{3-}$, dissociative short chain fatty acids may be mentioned. Examples of the material generating $OH^-$ include sodium hydroxide and the like; examples of the material generating $SO_4^{2-}$ include sodium sulfate and the like; examples of the material generating $PO_4^{3-}$ include sodium phosphate and the like; and examples of the material generating dissociative short chain fatty acid include caprylic acid ($CH_3(CH_2)_6COOH$) and the like.

The conditions for treating the negatively charged complex with cations are not particularly limited, but the temperature is usually 10 to 40° C., and preferably 20 to 30° C.; the pH is usually 6.5 to 8.0, and preferably 7.0 to 7.5; and the time is usually 1 to 20 minutes, and preferably 5 to 10 minutes. The solvent used for the cation treatment is not particularly limited as long as it is an aqueous solution, and for example, HEPES buffer solution and the like can be used. The amount of the cation to be added to the solvent can be appropriately controlled depending on the properties of the cation and the like, but the amount is typically 50-fold the amount of the lipid (moles of cation/moles of lipid) or greater.

The conditions for treating the positively charged complex with anions are not particularly limited, but the temperature is usually 10 to 40° C., and preferably 20 to 30° C.; the pH is usually 6.5 to 8.0, and preferably 7.0 to 7.5; and the time is usually 1 to 20 minutes, and preferably 5 to 10 minutes. The solvent used for the anion treatment is not particularly limited as long as it is an aqueous solution, and for example, HEPES buffer solution and the like can be used. The amount of the anion to be added to the solvent can be appropriately controlled depending on the properties of the anion and the like, but the amount is typically 50-fold the amount of the lipid (moles of anion/moles of lipid) or greater.

When the negatively charged complex is treated with cations, the negative charge on the surface of the negatively charged SUV type liposomes that are electrostatically bound to the positively charged particle is lost, and the hydrophobicity of the surface of the negatively charged SUV type liposomes increases, thus leading to membrane fusion between adjacent negatively charged SUV type liposomes, and the positively charged particle being coated with two sheets of lipid membrane. Also, when the positively charged complex is treated with anions, the positive charge on the surface of the positively charged SUV type liposomes that are electrostatically bound to the negatively charged particle is lost, and the hydrophobicity of the surface of the positively charged SUV type liposomes increases, thus resulting in membrane fusion between adjacent positively charged SUV type liposomes, and the negatively charged particle being coated with two sheets of lipid membrane. Thus, two sheets of lipid membrane coating the positively charged or negatively charged particle are newly formed on the external side of the positively charged or negatively charged particle, but at this time, the two sheets of lipid membrane are formed such that a space is formed therebetween.

When an aggregate of an object material is used as the positively charged or negatively charged particle, a bilamellar liposome encapsulating the aggregate of object material and having a space formed between the two sheets of lipid membrane which coat the aggregate of object material is produced. When an n-lamellar liposome, wherein n is an integer of 1 or greater, is used as the positively charged or negatively charged particle, an (n+2)-lamellar liposome having a space formed between the two sheets of lipid membrane which coat the n-lamellar liposome is produced.

The liposome obtained by coating a positively charged particle with two sheets of lipid membrane using the first method of the present invention is typically negatively charged. However, depending on the magnitude of the zeta potential of the negatively charged complex, type of the cation or the like, it is conceived that the liposome could be positively charged. The liposome obtained by coating a negatively charged particle with two sheets of lipid membrane using the second method of the present invention is typically positively charged. However, depending on the magnitude of the zeta potential of the positively charged complex, type of the anion or the like, it is conceived that the liposome could be negatively charged.

When a positively charged liposome is obtained by coating a positively charged or negatively charged particle with two sheets of lipid membrane using the first or second method of the present invention, the resulting positively charged liposome can be used as the positively charged particle for the first method of the present invention. When a negatively charged liposome or neutral liposome is obtained, the surface of the resulting negatively charged liposome or neutral liposome is modified with a cationic material to prepare a positively charged liposome, and the prepared positively charged liposome can be used as the positively charged particle for the first method of the present invention. As such, by repeatedly performing the first and/or second method of the present invention, a multilamellar liposome can be produced while controlling the number of lipid membranes.

When a negatively charged liposome is obtained by coating a positively charged or negatively charged particle with two sheets of lipid membrane using the first or second method of the present invention, the resulting negatively charged liposome can be used as the negatively charged particle for the second method of the present invention. When a positively charged liposome or neutral liposome is obtained, the surface of the resulting positively charged liposome or neutral liposome is modified with an anionic material to prepare a negatively charged liposome, and the prepared negatively charged liposome can be used as the negatively charged particle for the second method of the present invention. As such, by repeatedly performing the first and/or second method of the present invention, two sheets of lipid membrane can be newly formed on the external side of the two sheets of lipid membrane that have been already formed, and a multilamellar liposome can be produced while controlling the number of lipid membranes. Additionally, when two sheets of lipid membrane are newly formed on the external side of the two sheets of lipid membrane that have been already formed, the space formed between the two sheets of lipid membrane that have been already formed and the corresponding two sheets of lipid membranes is retained.

The liposome obtained by coating a positively charged or negatively charged particle with two sheets of lipid membrane according to the first or second method of the present invention preferably encapsulates an object material. If the object material is a material (for example, nucleic acid, peptide, protein, drug, sugar, complex thereof, etc.) to be delivered into a cell or a nucleus, the liposome encapsulating the object material can be used as a vector for delivering the object material into the cell or the nucleus. The liposome encapsulating the object material can be obtained by using an aggregate of the object material as the positively charged or negatively charged particle, or by using an n-lamellar liposome encapsulating the object material as the positively charged or negatively charged particle. Furthermore, such liposome can be obtained by retaining the object material between the two sheets of lipid membrane that are newly formed on the external side of the positively charged or negatively charged particle (for example, by retaining a liquid containing the object material).

The organism species from which the cell to deliver the object material is derived is not particularly limited, and may be any of animals, plants, microorganisms and the like. However, the organism species is preferably an animal, and more preferably a mammal. Examples of the mammal include human, monkey, cattle, sheep, goat, horse, pig, rabbit, dog, cat, rat, mouse, guinea pig and the like. Furthermore, the type of the cell to deliver the object material is not particularly limited, and for example, a somatic cell, a reproductive cell, a stem cell, cultured cells thereof, and the like may be mentioned.

The liposome encapsulating the object material can be used, for example, in a state of dispersion liquid. For the dispersion solvent, for example, a buffer solution such as physiological saline, phosphate buffer solution, citrate buffer solution, acetate buffer solution, or the like can be used. The dispersion liquid may contain additives such as, for example, sugars, polyhydric alcohols, water-soluble polymers, non-ionic surfactants, antioxidants, pH adjusting agents, hydration promoters.

The liposome encapsulating the object material can be used either in vivo or in vitro. In the case of using the liposome in vivo, the route of administration may be administration by injection such as, for example, intravenous, intraperitoneal, subcutaneous, trans nasal or the like, and the dosage and frequency of administration can be appropriately controlled depending on the type or amount of the object material encapsulated in the liposome, or the like.

EXAMPLES

Example 1

(1) Formation of DNA/poly-L-lysine Complex

DNA and poly-L-lysine were respectively dissolved in 5 mM HEPES buffer (pH 7.4). The DNA used was a plasmid DNA (a plasmid DNA containing CMV promoter and luciferase gene connected downstream of the promoter, and having a total length of about 7 kbp). Subsequently, the DNA solution (0.1 mg/mL) and the poly-L-lysine solution (0.1 mg/mL) were mixed and stirred using a vortex at room temperature, to prepare a solution containing DNA/poly-L-lysine complex (DNA concentration 0.05 mg/mL). The DNA/poly-L-lysine complex thus prepared had a particle diameter of about 70 to 100 nm, and a zeta potential of about 30 to 40 mV. Additionally, the rheological diameter was measured according to a quasi-elastic light scattering method, and the zeta potential was analyzed by an electrophoretic light scattering spectrometer (ELS-8000) (hereinafter, in the same manner).

(2) Preparation of SUV Type Liposome

Egg yolk phosphatidylcholine/cholesterol succinate (9:2 (molar ratio)) was dissolved in 0.5 mL of chloroform, and the solution was placed in a glass test tube. The solvent was removed by blowing nitrogen gas, and then the residue was placed in a desiccator for 1 hour to be dried. The obtained lipid membrane (0.55 μmol) was hydrated in 1 mL of HEPES buffer solution which had been warmed to 25° C. in advance, and ultrasonicated in an ultrasonicating bath to peel off the lipid membrane. The lipid membrane was further subjected to ultrasonication by a probe type ultrasonicator for 10 minutes to prepare SUV type liposomes. The SUV type liposome thus prepared had a particle diameter of about 50 to 100 nm, and a zeta potential of about −30 mV.

Fluorescence labeling of the SUV type liposome was carried out by introducing rhodamine (red) or NBD (4-nitrobenzo-2-oxa-1,3-diazole)-labeled dioleoylphosphatidylethanolamine (blue). Here, rhodamine as an aqueous phase marker was dissolved (10 mM) in the solvent for hydrating the lipid membrane, while the NBD-labeled lipid as a lipid marker was dissolved (0.1 mol % based on the total lipids) in a chloroform solution.

(3) Coating of DNA/poly-L-lysine Complex by Lipid Membrane

500 μL of the SUV type liposome was added to 250 μL of the solution containing DNA/poly-L-lysine complex to bring the two solutions into contact. In this way, it is believed that a complex containing the DNA/poly-L-lysine complex, and a plurality of SUV type liposomes that were electrostatically bound to the DNA/poly-L-lysine complex was formed. This complex had a particle diameter of about 500 to 3000 nm, and a zeta potential of about −30 mV. Additionally, the contacting was performed at room temperature (about 25° C.) for 5 minutes.

After the contacting, 55 μL of 0.1 N hydrochloric acid was added to treat the complex with $H^+$. In this way, it is believed that the negative charge on the surface of the SUV type liposomes which were electrostatically bound to the DNA/poly-L-lysine complex was lost, and the hydrophobicity of the surface of the SUV type liposomes increased, thus resulting in membrane fusion between the SUV type liposomes. The particle diameter after the $H^+$ treatment was about 85 to 130 nm, and the zeta potential was about −20 to −40 mV. As the particle diameter was reduced by the $H^+$ treatment, it was indicated that membrane fusion was induced between the SUV type liposomes which were electrostatically bound to the DNA/poly-L-lysine complex, the DNA/poly-L-lysine complex was coated with lipid membranes, and a liposome encapsulating the DNA/poly-L-lysine complex was formed.

The suspension after the $H^+$ treatment was subjected to lamination on a discontinuous sucrose density gradient (0, 30, 60%), and ultracentrifugation was performed under the conditions of 20° C. and 160,000 g for 2 hours. Fractions of 1 mL each were recovered from the upper portion, and the fluorescence intensity was measured. Among the fractions recovered by discontinuous sucrose density gradient ultracentrifugation, a fraction having a high DNA content was taken as the liposome-containing fraction. The liposome-containing fraction could be recovered from the boundaries of 30 to 60% of sucrose.

Example 2

In the same manner as in Example 1, a DNA/poly-L-lysine complex was coated with lipid membranes, and a liposome encapsulating the DNA/poly-L-lysine complex (hereinafter, referred to as "the first liposome") was prepared. Here, a liposome which was fluorescent-labeled with an NBD-labeled lipid (blue) was used as the SUV type liposome.

12 μL of a 1 mg/mL stearylated octaarginine solution was added to the external solution of the first liposome, and the mixture was left to stand at room temperature for 30 minutes to introduce octaarginine (5 mol % based on the total lipids) onto the surface of the first liposome (hereinafter, referred to as "the second liposome"). In addition, although the zeta potential of the first liposome was negative (about −30 mM), the zeta potential of the second liposome which was obtained by introducing octaarginine onto the surface of the first liposome was positive (about 30 to 50 mV).

In the same manner as in Example 1, SUV type liposomes (particle diameter: about 50 to 100 nm, zeta potential: about −30 mV, lipid concentration: 0.55 mM, amount added: 1.5 mL) were added to the solution containing the second liposome (0.37 mM, 750 μL), to bring the two solutions into contact. In this way, it is believed that a complex containing the second liposome and a plurality of SUV type liposomes that were electrostatically bound to the second liposome was formed. Here, a liposome whose internal aqueous phase was fluorescent-labeled with rhodamine was used as the SUV type liposome. The formed complex had a particle diameter of about 340 to 1500 nm and a zeta potential of about −30 mV.

After the contacting, 165 μL of 0.1 N hydrochloric acid was added to treat the complex with $H^+$. In this way, it is believed that the negative charge on the surface of the SUV type liposomes which were electrostatically bound to the second liposome was lost, and the hydrophobicity of the surface of the SUV type liposomes increased, thus resulting in membrane fusion between adjacent SUV type liposomes. The particle diameter after the $H^+$ treatment was about 170 to 240 nm, and the zeta potential was about −60 mV. Since the particle diameter was reduced by the $H^+$ treatment, it was shown that membrane fusion was induced between the SUV type liposomes which were electrostatically bound to the second liposome, and the second liposome was coated with lipid membranes.

The suspension after the $H^+$ treatment was subjected to lamination on a discontinuous sucrose density gradient (0, 5, 30%), and ultracentrifugation was performed under the conditions of 20° C. and 160,000 g for 2 hours. Fractions of 1 mL each were recovered from the upper portion. The respective DNA contents of the fractions were measured by DNA agarose gel electrophoresis (see FIG. 1(a)), and also the fluorescence intensities of rhodamine and NBD were measured to calculate the rhodamine contents and the NBD contents (see FIG. 1(b)).

Among the fractions recovered by discontinuous sucrose density gradient ultracentrifugation, a fraction having a high DNA content (fraction 11) was taken as the liposome-containing fraction. The liposome-containing fraction could be recovered from the boundaries of 5 to 30% of sucrose.

Furthermore, since NBD, rhodamine and DNA were present together, it was shown that for the liposome-containing fraction, the SUV type liposomes were fused while retaining the internal aqueous phase containing rhodamine, and for the liposome after fusion, a space in which the internal aqueous phase containing rhodamine was retained was formed.

Moreover, in the liposome-containing fraction, no fluorescent energy transfer was observed between NBD and rhodamine. Since the lipid membrane of the second liposome contained an NBD-labeled lipid (blue), it was shown that the lipid membrane of the second liposome was not in contact with the internal aqueous phase containing rhodamine. That is, it was shown that the membrane fusion between the SUV type liposomes which were electrostatically bound to the second liposome resulted in coating of the second liposome with two sheets of lipid membranes, and retention of the internal aqueous phase containing rhodamine in the space between the two sheets of lipid membranes which were newly formed on the external side of the second liposome. Assuming that if the second liposome was coated with one sheet of lipid membrane by the membrane fusion between the SUV type liposomes which were electrostatically bound to the second liposome, it would be conceived that the internal aqueous phase containing rhodamine would be retained in between the lipid membrane of the second liposome and the lipid membrane formed on the external side of the second liposome; but then, there would be observed fluorescent energy transfer between NBD and rhodamine. Also, assuming that if the lipid membrane of the second liposome and the lipid membrane of the SUV type liposomes fused by the membrane fusion between the SUV type liposomes which were electrostatically bound to the second liposomes (there is no change in the number of lipid membranes), it would be conceived that the internal aqueous phase containing rhodamine would be retained inside the second liposome; but then, there would be observed fluorescent energy transfer between NBD and rhodamine.

Example 3

A test was performed in the same manner as in Example 2, except that when coating the DNA/poly-L-lysine complex with lipid membranes to prepare a liposome encapsulating the DNA/poly-L-lysine complex (the first liposome), a liposome whose internal aqueous phase was fluorescent-labeled with rhodamine was used as the SUV type liposome, and that when forming a complex containing the second liposome and a plurality of SUV type liposomes that were electrostatically bound to the second liposome, a liposome which was fluorescent-labeled with an NBD-labeled lipid was used as the SUV type liposome.

Furthermore, from the results of Example 2, it is conceived that for the first liposome and the second liposome, the DNA/poly-L-lysine complex is coated with two sheets of lipid membrane, and the internal aqueous phase containing rhodamine is retained in between these two sheets of lipid membrane.

Figure 2:
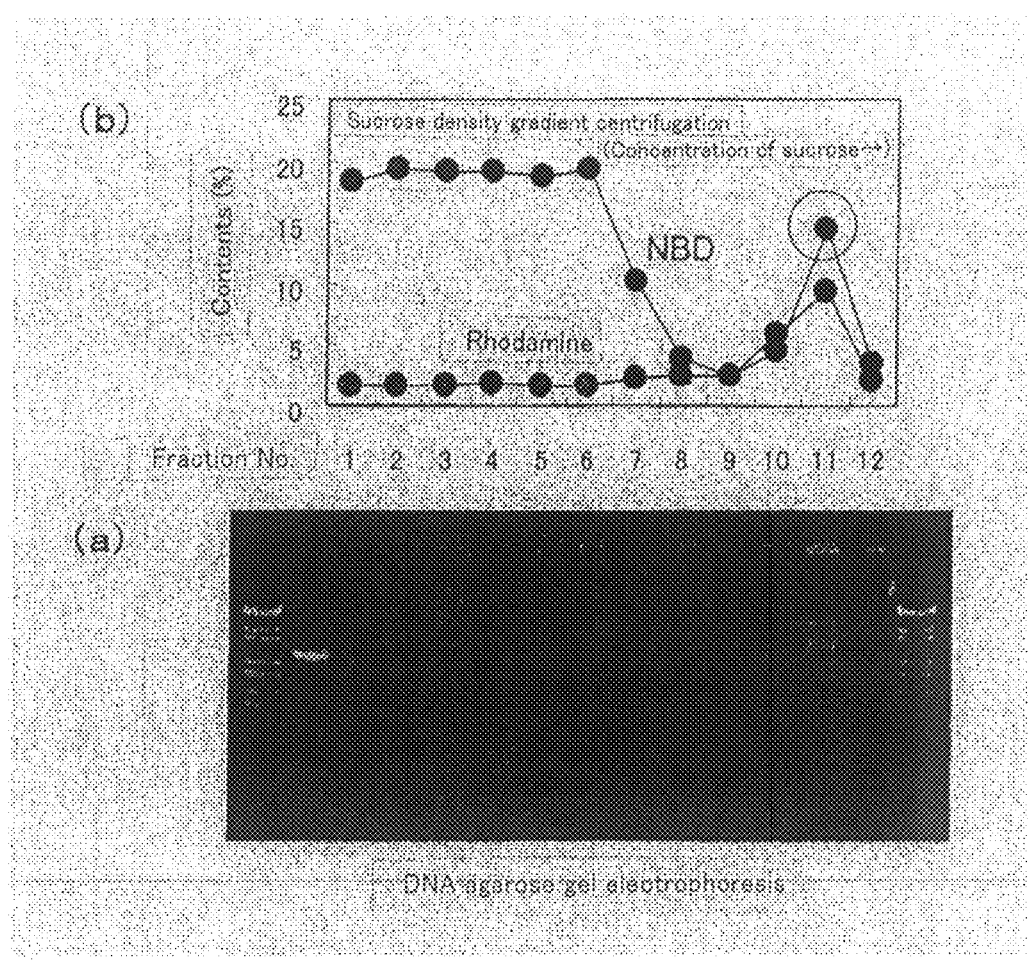
FIG. 2(a) is a photograph showing the results of measuring the DNA contents in each fraction by DNA agarose gel electrophoresis.
FIG. 2(b) is a graph showing the results of measuring the rhodamine contents and NBD contents in each fraction by means of fluorescence intensity.

The suspension after the $H^+$ treatment was subjected to lamination on a discontinuous sucrose density gradient (0, 5, 30%), and ultracentrifugation was performed under the conditions of 20° C. and 160,000 g for 2 hours. Fractions of 1 mL each were recovered from the upper portion. The respective DNA contents of the fractions were measured by DNA agarose gel electrophoresis (see FIG. 2(a)), and also the fluorescence intensities of rhodamine and NBD were measured to calculate the rhodamine contents and the NBD contents (see FIG. 2(b)).

Among the fractions recovered by discontinuous sucrose density gradient ultracentrifugation, a fraction having a high DNA content (fraction 11) was taken as the liposome-containing fraction. The liposome-containing fraction could be recovered from the boundaries of 5 to 30% of sucrose.

Furthermore, for the liposome-containing fraction, since NBD, rhodamine and DNA were present together, and no fluorescent energy transfer between NBD and rhodamine was observed, it was shown that when the SUV type liposomes that were electrostatically bound to the second liposome underwent membrane fusion, the space formed between the two sheets of lipid membrane for the second liposome (the space in which the internal aqueous phase containing rhodamine was retained) was retained.

Example 4

A DNA/poly-L-lysine complex was formed according to Example 1(1). For the DNA, as in Example (1), a plasmid DNA (a plasmid DNA containing CMV promoter and luciferase gene connected downstream of the promoter, and having a total length of 7037 bp (a product resulting from integration of luciferase gene into a pcDNA3.1 plasmid having CMV promoter)) was used.

According to Example 1(2), SUV type liposomes having lipid membranes comprising egg yolk phosphatidylcholine/cholesterol succinate (9:2 (molar ratio)) (hereinafter, referred to as "the first SUV type liposomes"), and SUV type liposomes having lipid membranes comprising dioleoylphosphatidylethanolamine/cholesterol succinate (9:2 (molar ratio)) (hereinafter, referred to as "the second SUV type liposomes") were prepared.

According to Example 1(3), a DNA/poly-L-lysine complex was coated using the first SUV type liposomes to prepare liposome A (bilamellar). Also, a DNA/poly-L-lysine complex was coated using the second SU liposomes to prepare liposome B (bilamellar) Furthermore, the liposome A was coated with lipid membranes using the second SUV type liposomes, to prepare liposome C (tetralamellar). Also, the liposome B was coated with lipid membranes using the first SUV type liposomes, to prepare liposome D (tetralamellar).

12 μL of a 1 mg/mL stearylated octaarginine solution was added to the external solutions of the liposomes A to D, and the mixtures were left to stand at room temperature for 30 minutes so as to introduce octaarginine (5 mol % based on the total lipids) onto the surface of each of the liposomes. Additionally, by introducing octaarginine onto the surface of each of the liposomes, the intracellular transfer path for all liposomes was unified (macropinocytosis).

0.25 mL of non-serum-containing DMEM medium in which the respective liposomes (equivalent to 0.4 μg of DNA) were suspended, was added to NIH3T3 cells ($4 \times 10^4$ cells/well) which were cultured in a 24-well plate, and the plate was incubated at 37° C. for 3 hours. After 3 hours, 1 mL of a medium containing 10% bovine fetal serum was added thereto, and the plate was incubated for 45 hours. Thereafter, the cells were lysed, a luciferase activity measuring reagent (luciferase assay system, Promega Corp.) was added to the cell lysate, and the luciferase activity was measured using a luminometer (Luminescencer PSN, ATTO). The mass of proteins in the cell lysate was measured using a BCA protein quantitative analysis kit (PIERCE, Rockford (Ill.).

Figure 3:
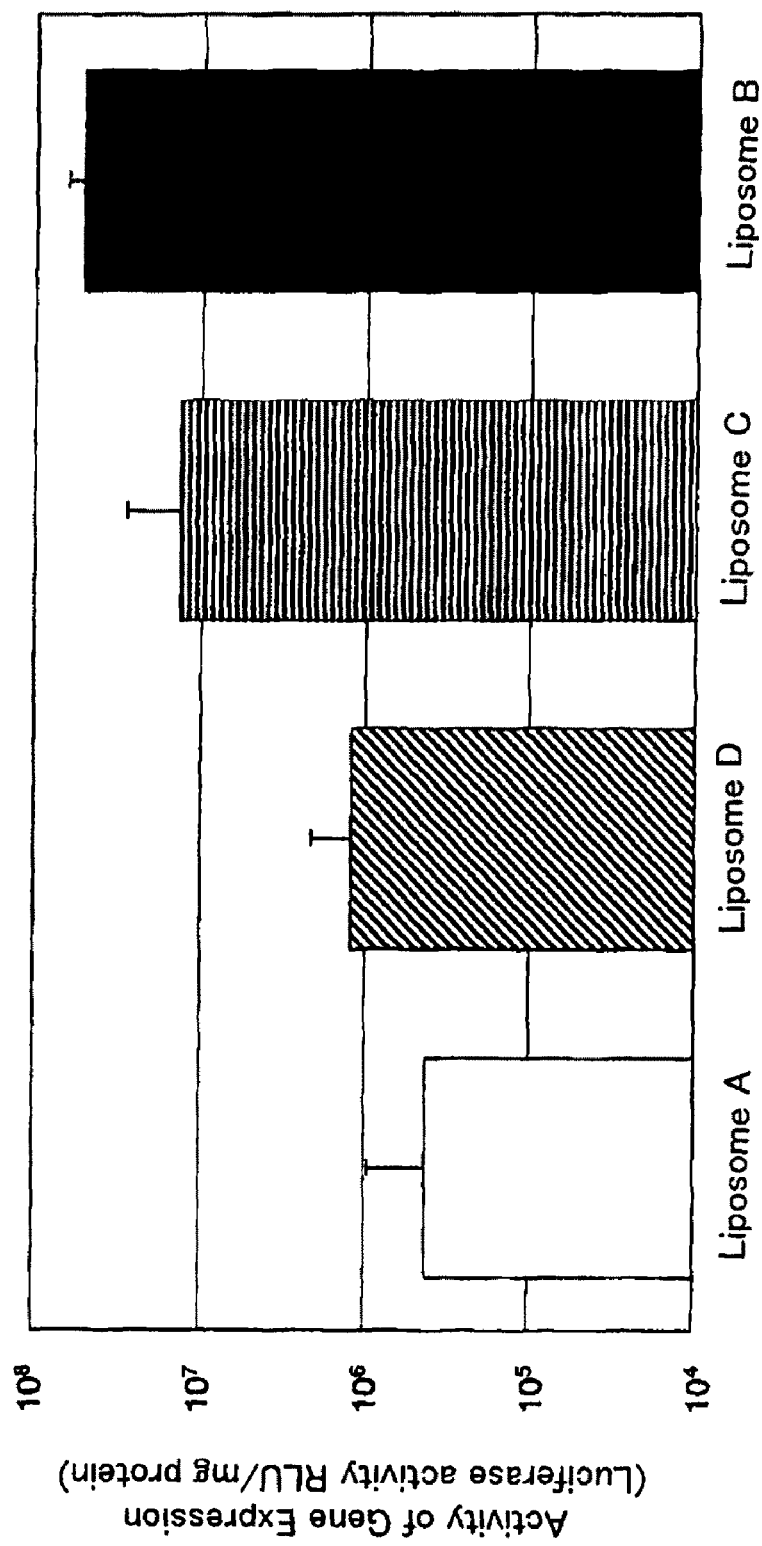
FIG. 3 is a graph showing the activity of expression of luciferase gene introduced into cells by various multilamellar liposomes.

The results are presented in FIG. 3. AS shown in FIG. 3, it was shown that the function of the liposomes (capability of introducing genes) was changed by changing the composition, number and the like of the lipid membranes constituting the liposomes.

The invention claimed is:

1. A method for coating a positively charged particle with two sheets of lipid membrane, the method comprising contacting the positively charged particle with a plurality of negatively charged SUV type liposomes, forming a negatively charged complex containing the positively charged particle and the negatively charged SUV type liposomes that are electrostatically bound to the positively charged particle, and treating the negatively charged complex with cations; wherein the positively charged particle is a positively charged n-lamellar liposome, wherein n is an integer of 1 or greater.

2. The method according to claim 1, wherein the positively charged particle has a zeta potential of 20 to 30 mV, while the negatively charged SUV type liposomes have a zeta potential of −20 to −30 mV.

3. The method according to claim 1, wherein the positively charged particle has a particle diameter of 50 nm or greater.

4. A liposome obtained by the method according to claim 1.

* * * * *